(12) United States Patent
Stern et al.

(10) Patent No.: US 11,871,934 B2
(45) Date of Patent: Jan. 16, 2024

(54) CATHETER WITH IMPROVED FLOW CHARACTERISTICS

(71) Applicant: MicroVention, Inc., Aliso Viejo, CA (US)

(72) Inventors: George Stern, Aliso Viejo, CA (US); Vladimir Satchouk, Aliso Viejo, CA (US)

(73) Assignee: MicroVention, Inc., Aliso Viejo, CA (US)

(*) Notice: Subject to any disclaimer, the term of this patent is extended or adjusted under 35 U.S.C. 154(b) by 80 days.

(21) Appl. No.: 17/488,052

(22) Filed: Sep. 28, 2021

(65) Prior Publication Data

US 2022/0096095 A1 Mar. 31, 2022

Related U.S. Application Data

(60) Provisional application No. 63/084,944, filed on Sep. 29, 2020.

(51) Int. Cl.
*A61M 25/00* (2006.01)
*A61B 17/12* (2006.01)

(52) U.S. Cl.
CPC ..... *A61B 17/12186* (2013.01); *A61M 25/007* (2013.01); *A61M 25/0071* (2013.01); *A61M 2025/0073* (2013.01)

(58) Field of Classification Search
CPC ..... A61B 17/12186; A61B 2017/1205; A61M 25/007; A61M 25/0071; A61M 2025/0073; A61M 2025/0098
See application file for complete search history.

(56) References Cited

U.S. PATENT DOCUMENTS

| | | | | |
|---|---|---|---|---|
| 6,808,510 B1* | 10/2004 | DiFiore | ............ | A61M 25/0069 604/523 |
| 2016/0114123 A1* | 4/2016 | Cully | ............... | A61M 25/0026 604/524 |
| 2017/0368306 A1* | 12/2017 | Tal | .................... | A61M 25/0067 |

* cited by examiner

*Primary Examiner* — Amber R Stiles
*Assistant Examiner* — Nelson Louis Alvarado, Jr.
(74) *Attorney, Agent, or Firm* — Inskeep IP Group, Inc.

(57) ABSTRACT

Catheters are described that have improved flow characteristics that may be particularly helpful when delivering embolic agents within a blood vessel. One catheter includes a fluid flow modifier that is configured to create laminar fluid flow out of a distal end of the catheter to help reduce turbulence and achieve predictable fluid movement. Another catheter includes scavenging ports that are configured to suction in embolic agents that have refluxed proximally back from a distal end of the catheter.

18 Claims, 9 Drawing Sheets

CATHETER WITH IMPROVED FLOW CHARACTERISTICS

RELATED APPLICATIONS

This application claims benefit of and priority to U.S. Provisional Application Ser. No. 63/084,944 filed Sep. 29, 2020 entitled Flow Straightener Catheter, which is hereby incorporated herein by reference in its entirety.

BACKGROUND OF THE INVENTION

Embolic delivery catheters are generally used to deliver embolic agents or devices (e.g., embolic beads or liquid embolic agent) into the vessels of a patient to cause therapeutic blockage. For example, such catheters may be used to occlude blood supplying a vessel, to occlude an arteriovenous malformation, or to occlude a vascular malformation such as an aneurysm.

One challenge to embolization procedures is the difficulty of delivering agents in the presence of turbulent blood flow and/or turbulence created by the delivery media. This turbulence can disrupt or push away the embolic material or radio contrast agents from its intended target position.

One access catheter used for delivery of embolic devices can be found in U.S. Pat. No. 10,398,875, the contents of which are incorporated by reference herein. This patent describes the use of a microcatheter tip that has pores on the sidewalls to reduce backflow of embolic agents during delivery and has been used for Guerbet International's Sequre Microcatheter. As fluid is pushed out the main delivery opening, fluid also is pushed out the side pores to make it difficult for embolic agents to move proximally beyond these side fluid jets. One disadvantage of this design is the expectation that significant backflow and turbulence will still be generated away from a target delivery area during delivery of the embolic agents, which can lead to less accurate and predictable delivery of embolic material.

Hence, there is a need for catheter designs and techniques that help resist this turbulence during delivery and achieve more accurate and predictable delivery of embolic material. There is also a need for catheter designs and techniques that help limit or capture any embolic material that has proximally migrated away from a target area.

SUMMARY OF THE INVENTION

One embodiment of this specification is directed to a fluid flow modifier located at or near the distal end of a catheter shaft to create laminar from a delivery lumen of the catheter. This can be used, for example, to straighten and/or improve the cohesiveness of the fluid flow after exiting the catheter. In fluid dynamics, laminar flow is generally characterized by fluid particles following paths in layers, with each layer moving smoothly past the adjacent layers with little or no mixing. At relatively low velocities, the fluid tends to flow without substantial lateral mixing, and adjacent layers slide past one another like playing cards.

In one embodiment, the fluid flow modifier of the catheter shaft may form a fluid flow that has a cross sectional area with an inner diameter sufficient for embolic material, radio-contrast agents, or similar material, and as well as a cross-sectional area that circumferentially surrounds the inner diameter area as a separate laminar flow. In other words, an outer circumferential curtain of fluid is created around an inner flow in a laminar manner. Alternately, a plurality of smaller discrete laminar streams may surround the inner diameter. These laminar flow lines or areas around inner diameter area help reduce the amount of potential turbulence encountered with any embolic devices that have been ejected from the distal tip of the catheter shaft and therefore may provide more predictable delivery to a desired target location.

While this improved flow may be helpful for any type of catheter used for delivering fluid within a patient, it can be particularly helpful for catheters configured to deliver embolic agents. For example, rapidly solidifying liquid embolic agents, embolic spheres/pellets, or embolic coils. This improved flow may also be helpful for delivering a liquid contrast agent into a patient's vessels, with or without an embolic agent. Hence, while use with embolic agents and contrast are specifically discussed herein, use for delivery of other fluids is specifically contemplated.

In one embodiment, the fluid flow modifier comprises a distal region of the catheter that branches out into a central or middle lumen and a plurality of smaller channels or lumens surrounding the middle lumen. These lumens can be fully enclosed throughout most of their length or can include a longitudinal channel along its length that connects with the middle lumen. As fluid exits these lumens, it creates one or more smaller laminar flows that circumferentially surround a larger middle flow.

In another embodiment, a distal region of the catheter that branches out into a central or middle lumen and a plurality of smaller open lumens surrounding the middle lumen but remain open to or in communication with the middle lumen via a connecting channel.

Another embodiment of this specification is directed to a delivery catheter that can not only inject embolic beads (or other embolic materials) out its main lumen but can suction or draw up embolic beads that have refluxed proximally away from a target location through smaller sidewall apertures in the catheter's sidewall. This may prevent the embolic beads from moving proximally beyond the sidewall apertures.

In one example, suction or vacuum force through sidewall apertures of the catheter is achieved by increasing the speed of the fluid when passing through the catheter's lumen adjacent to the sidewall apertures (i.e., increasing the speed relative to the fluid speed proximally in the catheter's lumen). This increase in speed at a location within the lumen also results in a decrease in pressure as the speed decreases, which causes a vacuum or suction force relative to the pressure outside of the catheter lumen and therefore draws fluid and other material from outside of the catheter into the sidewall apertures. This phenomenon is described by Bernoulli's principle or the Venturi effect and allows for the recapture or scavenging of embolic beads (or other embolic agents) that have refluxed or moved proximally. There, the embolic beads move back into the main lumen of the catheter where they can again be delivered to the target area. Hence, this suction on the side of the catheter helps prevent the embolic beads from migrating further proximally to undesirable areas of the vasculature.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements. While different embodiments are described, features of each embodiment can be used interchangeably with other described embodiments. In other words, any of the features of each of the embodiments can be mixed and matched with each other, and embodiments should not necessarily be rigidly interpreted to only include the features shown or described.

One embodiment of this specification is directed to a fluid flow modifier located at or near the distal end of a catheter shaft to create laminar from a delivery lumen of the catheter. This can be used, for example, to straighten and/or improve the cohesiveness of the fluid flow after exiting the catheter. In fluid dynamics, laminar flow is generally characterized by fluid particles following paths in layers, with each layer moving smoothly past the adjacent layers with little or no mixing (i.e., a multi-layered fluid flow). At relatively low velocities, the fluid tends to flow without substantial lateral mixing, and adjacent layers slide past one another like playing cards.

For example, the fluid flow modifier of the catheter shaft may form a fluid flow that has a cross sectional area with an inner diameter sufficient for passage of embolic material, radio-contrast agents, or similar material, and as well as a cross-sectional area that circumferentially surrounds the inner diameter area as a separate laminar flow. In other words, an outer circumferential curtain of fluid is created around an inner flow in a laminar manner. Alternately, a plurality of smaller discrete laminar streams may surround the inner diameter. These laminar flow lines or areas around inner diameter area help reduce the amount of potential turbulence encountered with any embolic devices that have been ejected from the distal tip of the catheter shaft and therefore may provide more predictable delivery to a desired target location.

While this improved flow may be helpful for any type of catheter used for delivering fluid within a patient, it can be particularly helpful for catheters configured to deliver embolic agents. For example, rapidly solidifying liquid embolic agents, embolic spheres/pellets, or embolic coils. This improved flow may also be helpful for delivering a liquid contrast agent into a patient's vessels, with or without an embolic agent. Hence, while use with embolic agents and contrast are specifically discussed herein, the use of the fluid flow modifier for delivery of other fluids is specifically contemplated.

The embodiments described in this specification generally describe the creation of laminar flow with an outer circumferential cross-sectional layer or plurality of streams surrounding an inner circular cross-sectional area. However, different variations of this arrangement are possible. For example, the total cross-sectional shape of the entire laminar flow need not be circular in their cross-sectional shape, but instead a fluid flow modifier can be configured such that it can form a triangular, square, rectangular, pentagonal, hexagonal, octagonal, or similar shape. In another example, more than two flow layers can be created (e.g., three or four concentric layers are possible). In a further example, the adjacent streams surrounding the inner circular cross-section can be connected without or with limited partition, creating a gradient of outer laminar flow to inner turbulent flow.

The lumens can be configured such that all flow layers are ejected from the catheter along a trajectory parallel to the longitudinal axis of the catheter or some lumens can be configured for a trajectory non-parallel to the longitudinal axis of the catheter. For example, the outer circumferential layer can be configured to bend radially inward or radially outward as it leaves the catheter, relative to the inner cross-sectional area.

Additionally, the lumens can be configured to form relatively uniform and smooth fluid streams or non-uniform streams. For example, the outer circumferential layer can be configured to have a rotational component so that it rotates or twists relative to the inner cross-sectional area, or vise-versa.

FIGS. 1-8 illustrate one embodiment of a catheter 100 that is configured to create laminar flow to improve the flow characteristics of the fluid being ejected from the catheter's distal end. This laminar flow of the ejected fluid can result in more predictable and cohesive flow within a patient's vessel that reduces backflow away from an intended target area.

The catheter 100 may have many different variations, but typically at least includes a catheter shaft 102 with a distal region 104 at a distal end of the catheter shaft 102 that includes a fluid flow modifier. The fluid flow modifier is one or more structures that are configured to create laminar flow between two or more fluid streams when fluid is advanced or pushed through the distal region 104 and out of the catheter 100, as discussed further below.

In fluid dynamics, laminar flow may be characterized by fluid particles following in smooth paths in layers, with each layer moving smoothly past the adjacent layers with little or no mixing. At low velocities, the fluid tends to flow without lateral mixing, and adjacent layers slide past one another like playing cards. There are typically no cross-currents perpendicular to the direction of flow, nor eddies or swirls of fluids. In laminar flow, the motion of the particles of the fluid tends to be relatively orderly with particles close to a solid surface moving in straight lines parallel to that surface.

When a fluid is flowing through a closed channel such as a tube or between two flat plates, either of two types of flow may occur depending on the velocity and viscosity of the fluid: laminar flow or turbulent flow. Laminar flow typically occurs at lower velocities, below a threshold at which the flow becomes turbulent. That velocity is determined by a dimensionless parameter characterizing the flow called the Reynolds number, which also depends on the viscosity and density of the fluid and dimensions of the channel. Turbulent flow is a less orderly flow regime that is characterized by eddies or small packets of fluid particles, which result in lateral mixing.

Figures 1, 2:
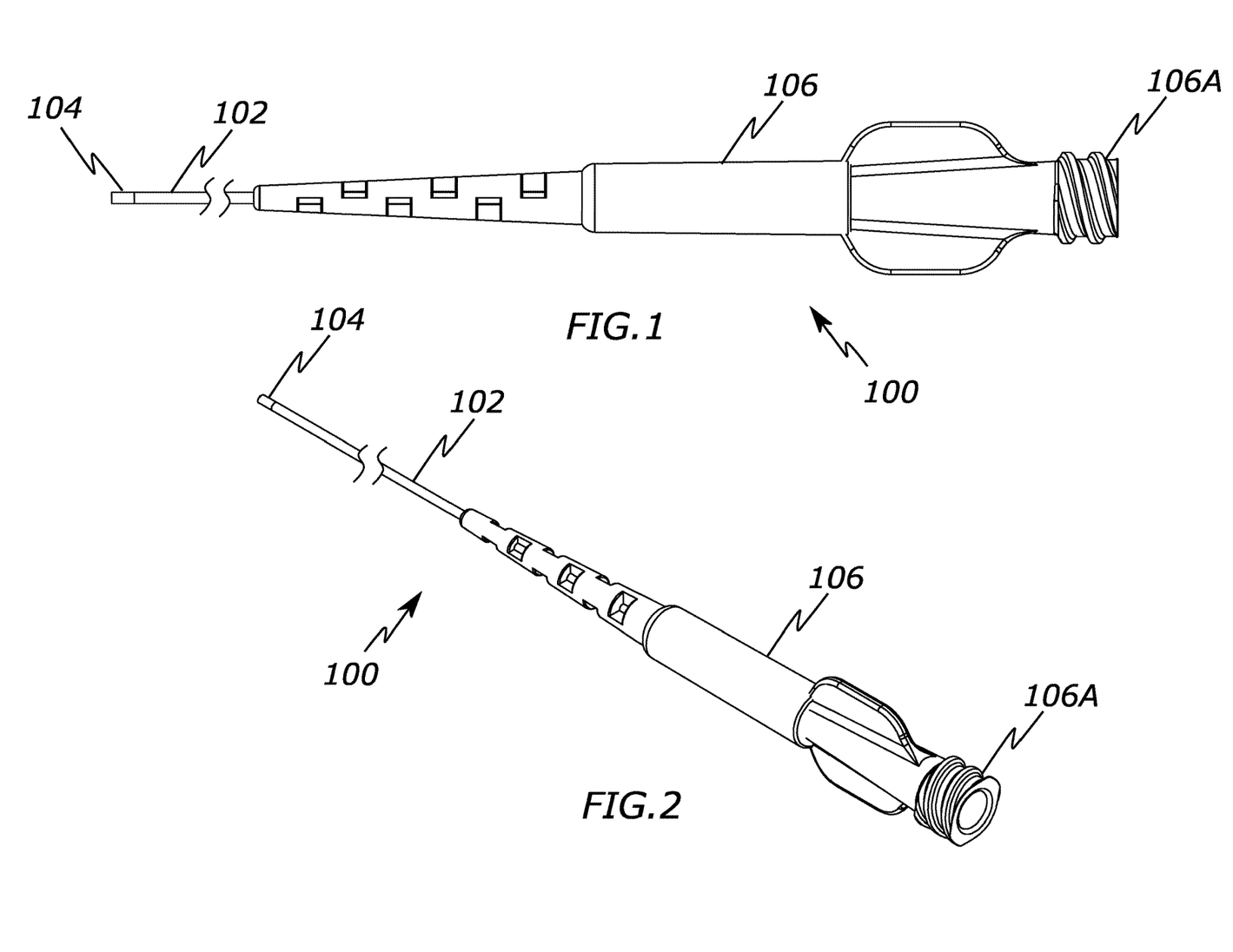
FIG. 1 is a side view of a catheter configured to create laminar fluid flow according to the present invention.
FIG. 2 is a perspective view of a catheter configure to create laminar fluid flow according to the present invention.
Figure 3:
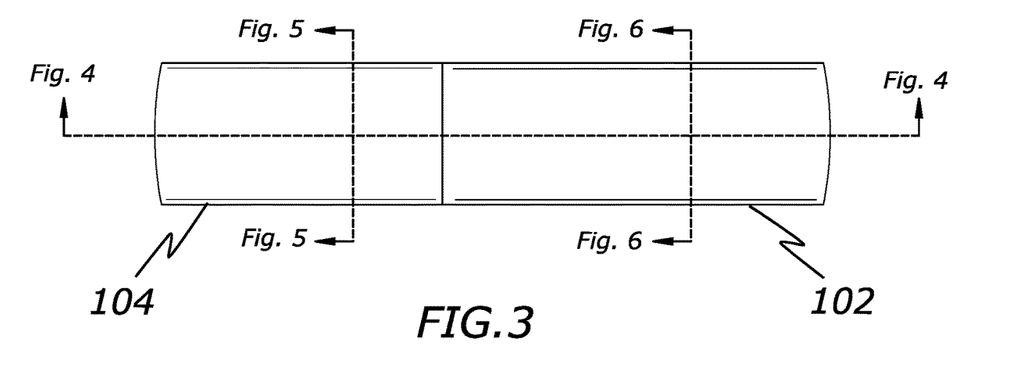
FIG. 3 is a side view of a distal end of a catheter configure to create laminar fluid flow according to the present invention.

The catheter shaft 102 typically will have a catheter hub 106 which facilitates connections to various other components, for example via a threaded portion 106A. Example components include an adapter (e.g., syringe adapter), a syringe, a contrast supply, or other known catheter components. The catheter hub includes at least one lumen therethrough that connects to a catheter shaft lumen 102A that extends the length of the catheter shaft and into the interior of the distal region 104. Hence, fluid and/or embolic agents introduced at the catheter hub 106 at the proximal end of the catheter can be advanced or injected through the catheter shaft lumen 102A, through the lumen of the distal portion 104, and out the lumen opening at the distal end of the catheter 100. While the catheter shaft 102 is depicted with a single lumen 102A, multiple lumens are also possible (e.g., inclusion of a separate guidewire lumen).

FIGS. 3-8 best illustrate the fluid flow modifier structures of the present embodiment located within the distal portion 104 of the catheter 100. While the fluid flow modifier structures are illustrated as only being included within the distal region 104 (e.g., about 1 cm to 10 cm from the distal edge of the catheter 100), the structures can extend proximally much further and even to the very proximal end of the shaft 102 or even into the lumen of the catheter hub 106. In some configurations it may even be possible to have the fluid flow modifying structures terminate proximal of the distal edge of the catheter 100, though generally positioning these structures at least at the very distal end of the catheter 100 is likely to achieve the desired laminar flow.

Generally, the fluid flow modifier structures of the present embodiment comprise a main middle lumen 104D and a plurality of smaller lumens 104C that are positioned circumferentially around the middle lumen 104D. Hence, as fluid passes through these lumens 104D and 104C, a larger, main fluid flow is created and a plurality of smaller fluid flows are created that circumferentially surround the main fluid flow in a laminar manner.

Figure 4:
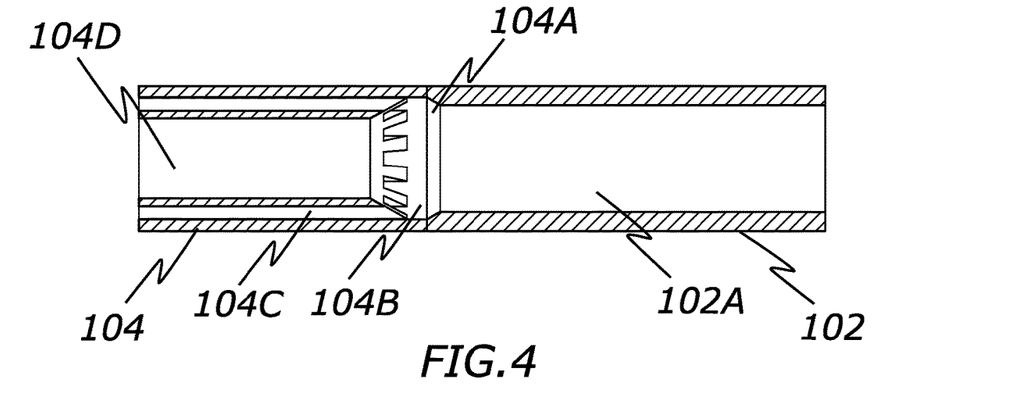
FIG. 4 is a cross-sectional view of FIG. 3 according to the present invention.
Figure 5:
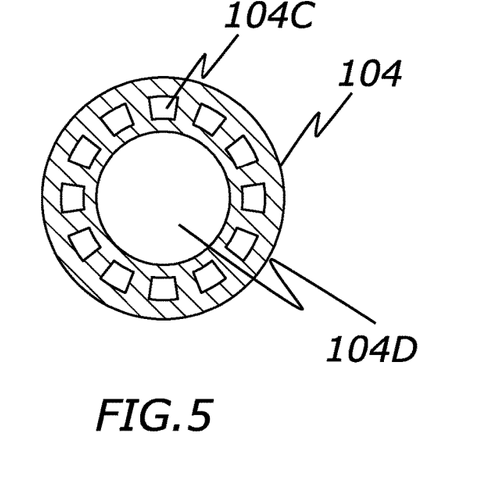
FIG. 5 is a cross-sectional view of FIG. 3 according to the present invention.
Figure 6:
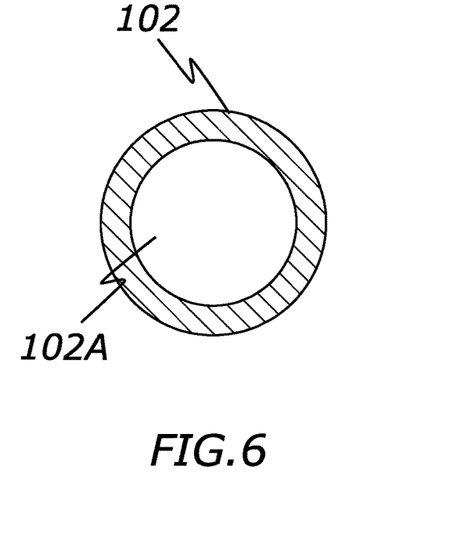
FIG. 6 is a cross-sectional view of FIG. 3 according to the present invention.
Figure 7:
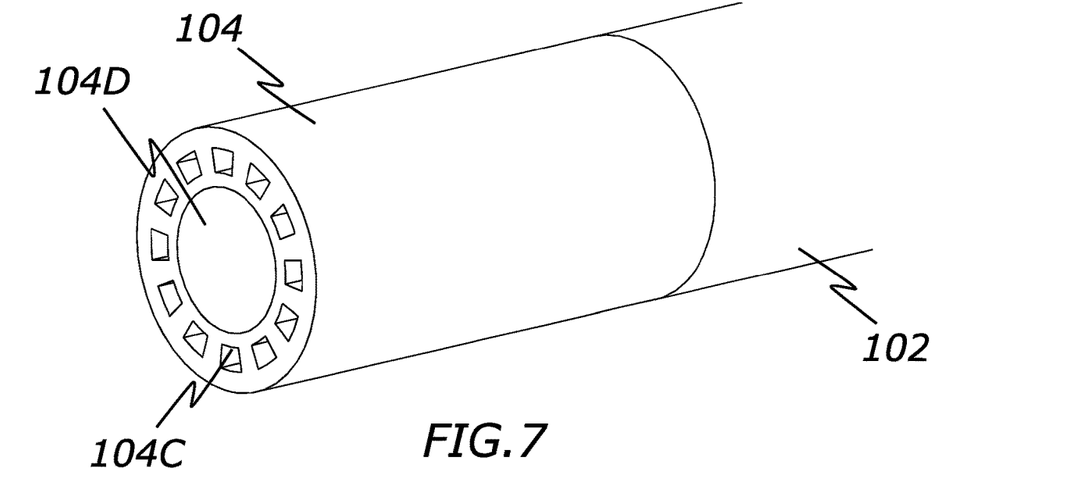
FIG. 7 is a perspective view of a distal end of a catheter configure to create laminar fluid flow according to the present invention.
Figure 8:
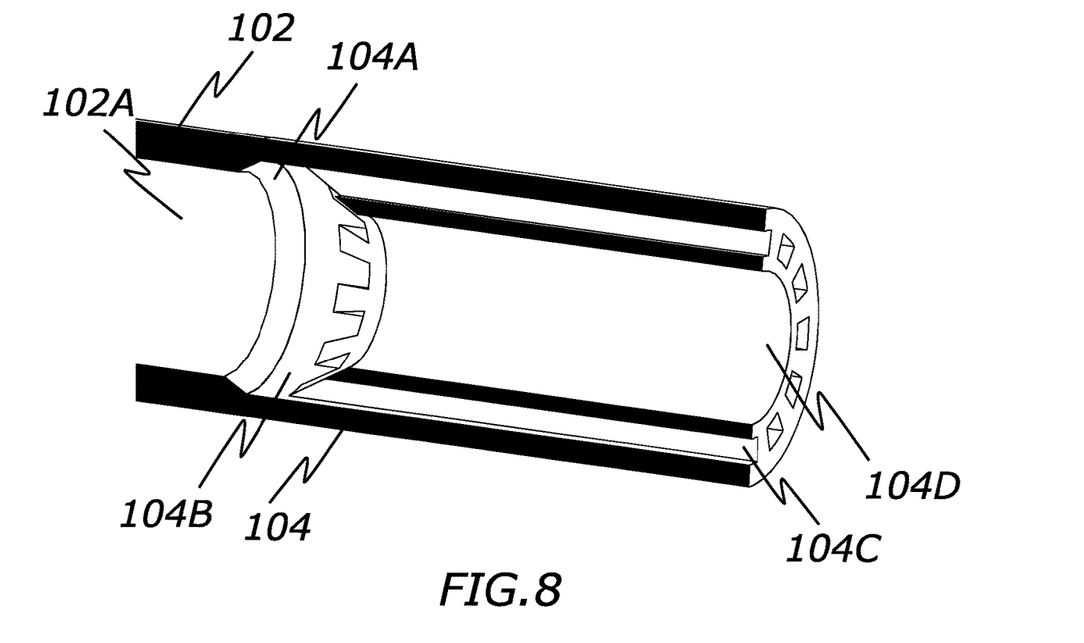
FIG. 8 is a cross sectional view of a distal end of a catheter configure to create laminar fluid flow according to the present invention.
Figures 9, 10:
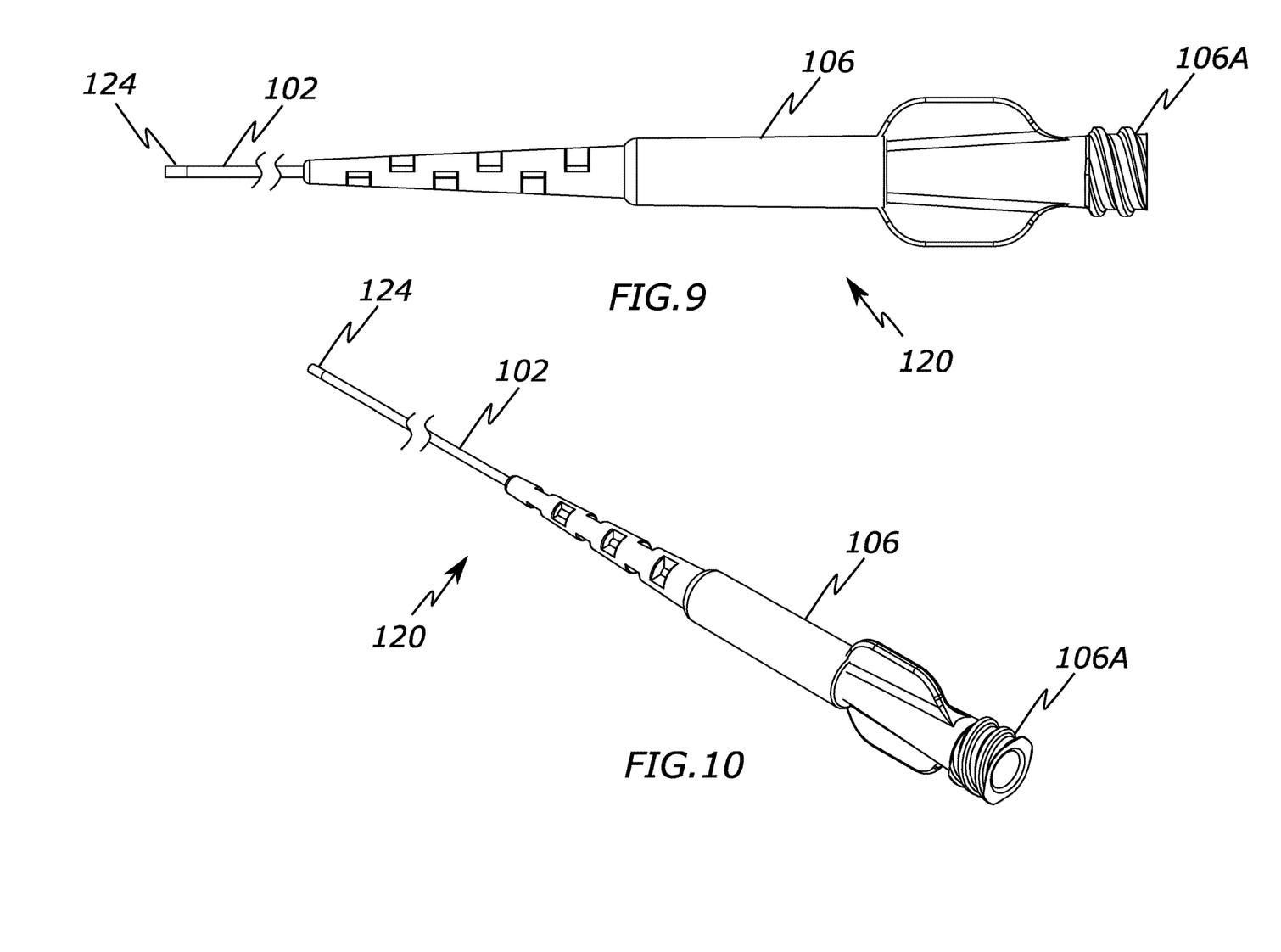
FIG. 9 is a side view of a catheter configured to create laminar fluid flow according to the present invention.
FIG. 10 is a perspective view of a catheter configure to create laminar fluid flow according to the present invention.
Figure 11:
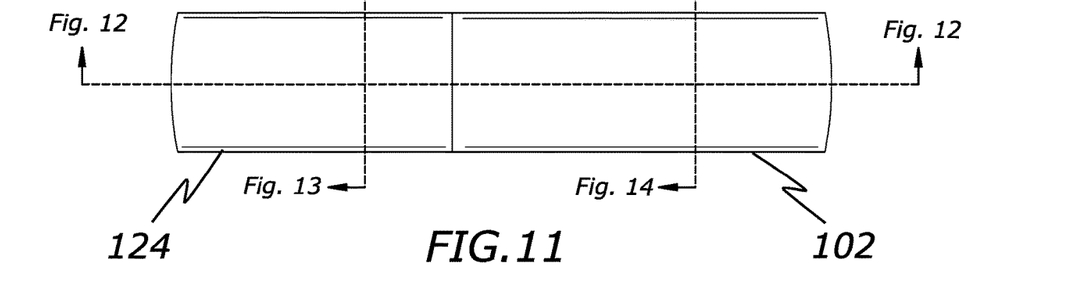
FIG. 11 is a side view of a distal end of a catheter configure to create laminar fluid flow according to the present invention.
Figure 12:
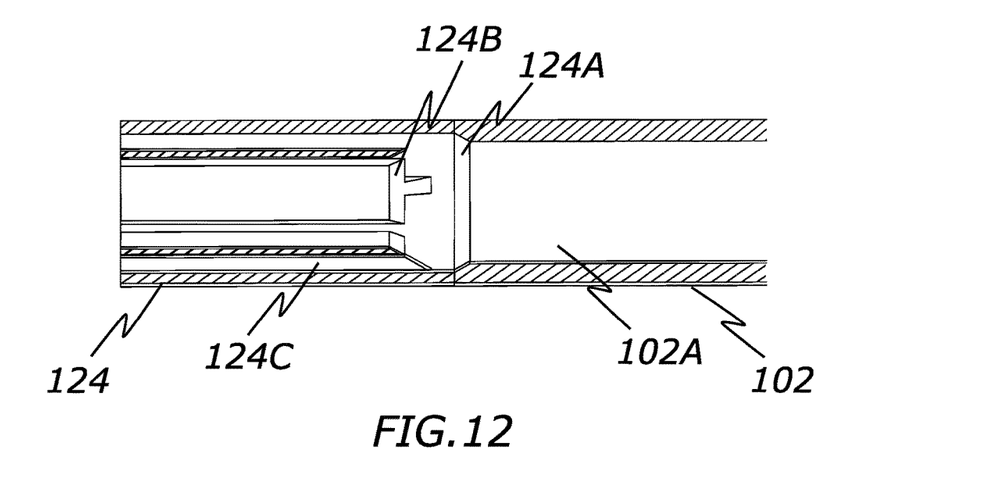
FIG. 12 is a cross-sectional view of FIG. 11 according to the present invention.
Figure 13:
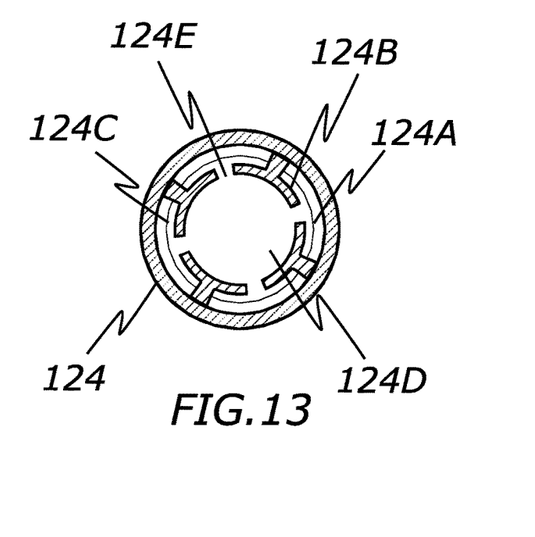
FIG. 13 is a cross-sectional view of FIG. 11 according to the present invention.
Figure 14:
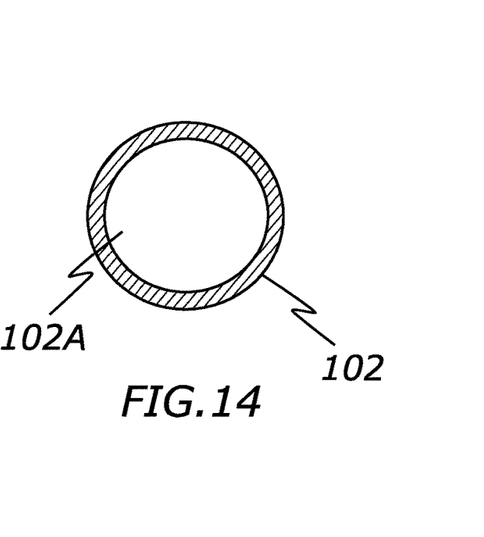
FIG. 14 is a cross-sectional view of FIG. 11 according to the present invention.
Figure 15:
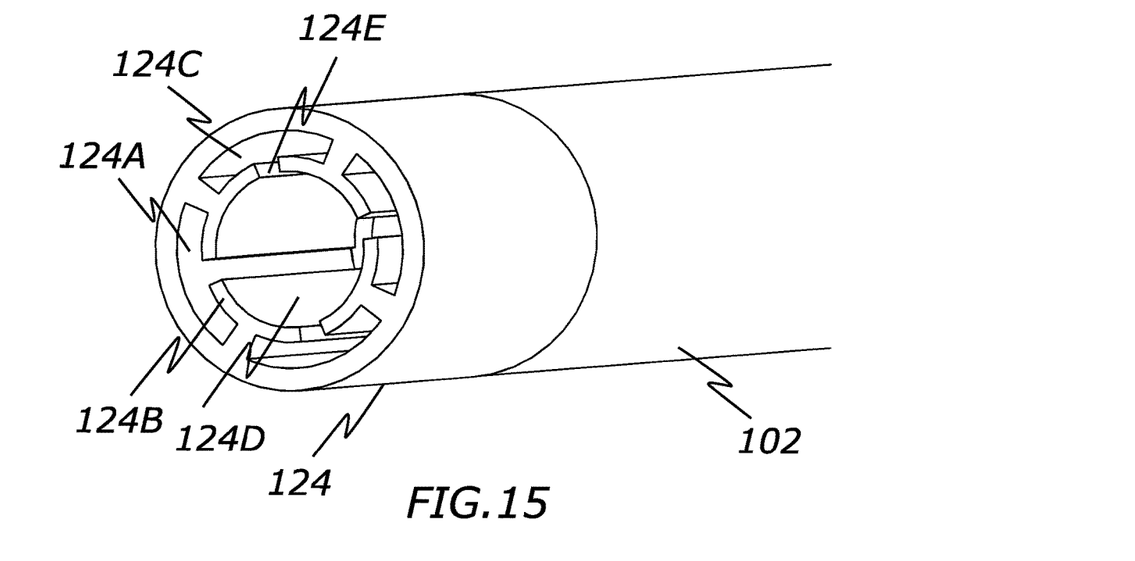
FIG. 15 is a perspective view of a distal end of a catheter configure to create laminar fluid flow according to the present invention.

A transition region between the catheter shaft lumen 102A and the lumens 104D and 104C can be included to better direct a desired amount and speed of the fluid through the distal region 104. For example, the catheter shaft lumen 102A may have a relatively constant or uniform diameter of a first size. As best seen in FIG. 4, a first tapered surface 104A may increase in diameter in the distal direction. A second tapered surface decreases in diameter in the distal direction, but also includes apertures into the plurality of lumens 104C, as well as a main center opening into the main middle lumen 104D. In this manner, the main middle lumen 104D has a somewhat smaller diameter than the catheter shaft lumen 102A and the plurality of lumens 104C have a much smaller diameter than both lumens 104D and 102A.

Both tapered surfaces 104A, 104B can be formed at various angles to increase or decrease the amount of fluid that may enter each. For example, a steeper angle may allow for more fluid to pass into lumens 104C. In one specific example, the tapered surfaces 104A, 104B can be tapered between 30-75 degrees relative to a longitudinal axis of the catheter shaft 100 and in distally increasing in diameter (taper 104A) or distally decreasing in diameter (taper 104B). In another example, a second gradual outward taper can be added after the first to the central lumen, minimizing the potential frictional loss in pressure going through the choke.

The size of the smaller diameter lumens 104C may also result in pressure differences relative to the middle lumen 104D and therefore differences in speed of the fluid. For example, fluid passing through the smaller diameter lumens 104C may have a higher speed than fluid passing through the middle lumen 104D and therefore may initially exit the catheter 100 first. This may initially create a plurality of fluid cylinder shapes that help maintain the trajectory of fluid from the middle lumen 104D and also limit or prevent any currents in the blood of the patient from interfering as well.

In one example, the diameter of the smaller diameter lumens 104C compared to the diameter of the middle lumen 104D may be a ratio between about 10% to 90%. In a specific example, the diameter of the smaller diameter lumens 104C is within an inclusive range of about 10% to 20% of the outer diameter, and the diameter of the middle lumen 104D is within an inclusive range of about 30% to 70% of the outer diameter.

The smaller diameter lumens 104C are depicted as being equally sized and spaced from each other and from the middle lumen 104D. However, the diameter of the lumens 104C may be different from each other and may have different spacing. For example, the diameter of the lumens 104C may alternate between relatively smaller and larger diameters, and/or alternate between being closer to and further from the middle lumen 104D. In another example, a second layer of intermediate size lumens may be positioned between the middle and outer smaller diameter lumens.

The smaller diameter lumens 104C and the middle lumen 104D are depicted as being relatively uniform and straight passages which may result in relatively uniform laminar flows being created as the fluid exits the catheter 100. However, the middle lumen 104D, the smaller diameter lumens 104C, or both may have walls that are not uniform and/or straight so as to impart specific movement on each part of the laminar flow.

For example, one or more of the lumens may have helical ridges or fins that impart a twisted flow to its component of the laminar flow. In another example, one or more of the lumens may have bumps or foil shapes near their distal exits. In yet another example, the smaller diameter lumens 104C may be oriented at a slightly different angle than that of middle lumen 104D so as to create an outer fluid curtain that increases or decreases in diameter as it flows out of the end of the catheter 100.

The present embodiment of the catheter 100 illustrates the middle lumen 104D with a circular cross-sectional shape and the smaller diameter lumens 104C with relatively square or trapezoid shapes. However, either lumens can have any combinations of cross-sectional shapes, such as circular, square, rectangular, arc-shaped, triangular, pentagonal, hexagonal, octagonal, or similar shapes.

While a plurality of smaller diameter lumens 104C are depicted, it is also possible to have one or more lumens 104C that extend much further around the middle lumen 104D. For example, a single lumen 104C can extend entirely around or can form a "C" shape and extend almost entirely around the middle lumen 104D. Alternately, two arc shaped lumens 104C can together extent entirely around the middle lumen 104D. In another example, 3 or 4 arch shaped lumens 104C can together extend entirely around the middle lumen 104D.

In the embodiment of the catheter 100, most or all of the middle lumen 104D is a separate discrete passage from the smaller diameter lumens 104C. In other words, the lumens are completely walled off from each other along most or all of their length. However, these lumens may also maintain a connection with each other along part of or all of their length, such as a via a longitudinal channel.

In that regard, FIGS. 9-16 illustrate another embodiment of a catheter 120 that is generally similar to the previously described catheter 100 but includes a distal portion 124 with lumens that remain connected to each other along their length.

Specifically, the distal portion 124 includes a middle lumen 124B and a plurality of smaller lumens 124C that surround the middle lumen 124D. The smaller lumens 124C are formed from a plurality of structures 124B that form a generally "T" shaped cross section with a curved or arced elongated top portion. The top portions of each structure 124B are spaced apart from adjacent structures 124B so as to create gaps or channels 124E connecting each of the lumens 124C with the middle lumen 124D. By creating these gaps or channels between the lumens, the lumen walls serve as a rectifier to reduce rotational turbulence.

The smaller lumens 124C are illustrated as having a rectangular arc shape, but any of the previously discussed cross sectional shapes can also be used, such as circular, square, rectangular, arc-shaped, triangular, pentagonal, hexagonal, octagonal, or similar shapes. Additionally, any of the other features discussed with regard to lumens 104C are applicable here, such as including shapes within the lumens 124C (e.g., helical fins) or having different angles relative to the middle lumen 124D.

Figure 16:
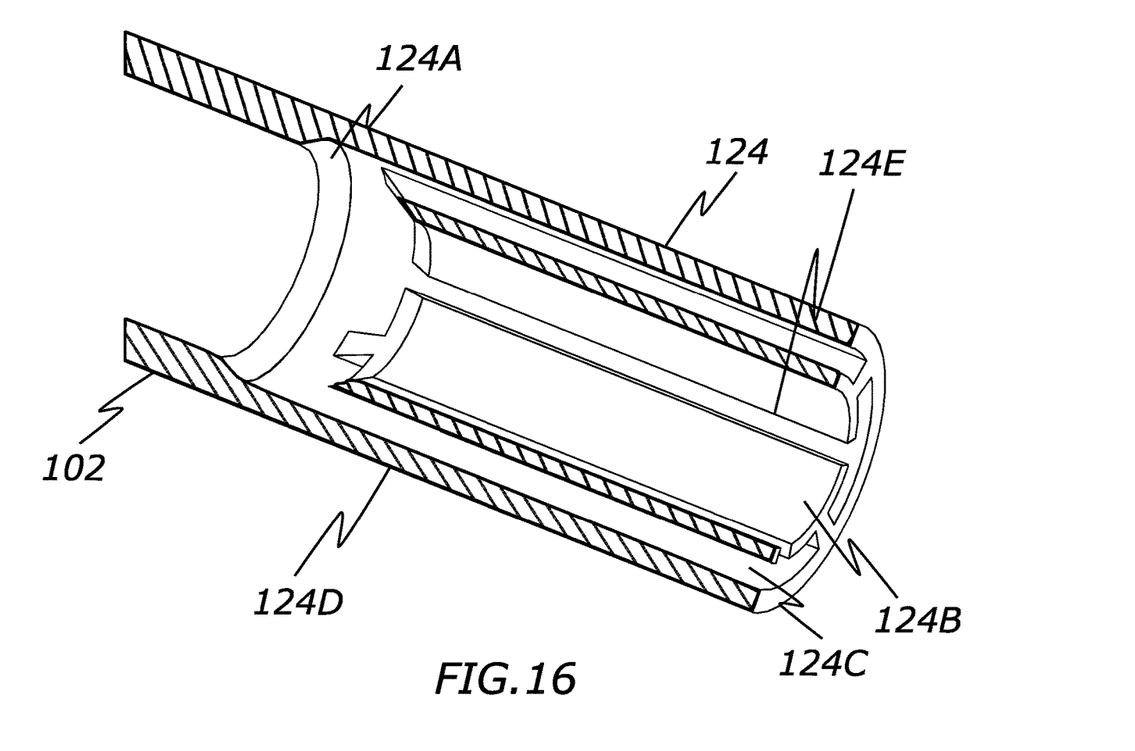
FIG. 16 is a cross sectional view of a distal end of a catheter configure to create laminar fluid flow according to the present invention.
Figure 17:
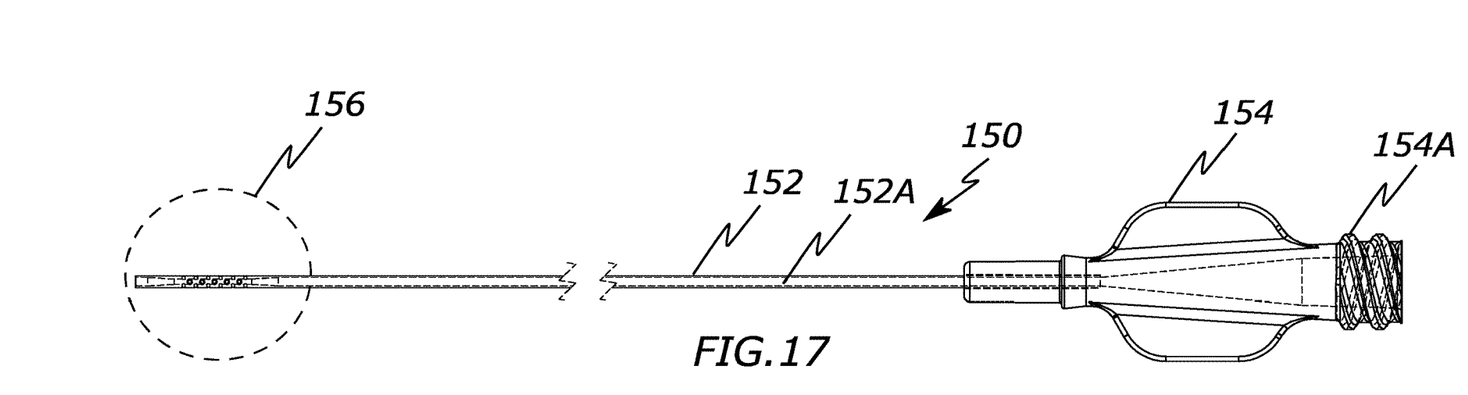
FIG. 17 is a side view of a catheter configured to create suction through side apertures at its distal end according to the present invention.
Figure 18:
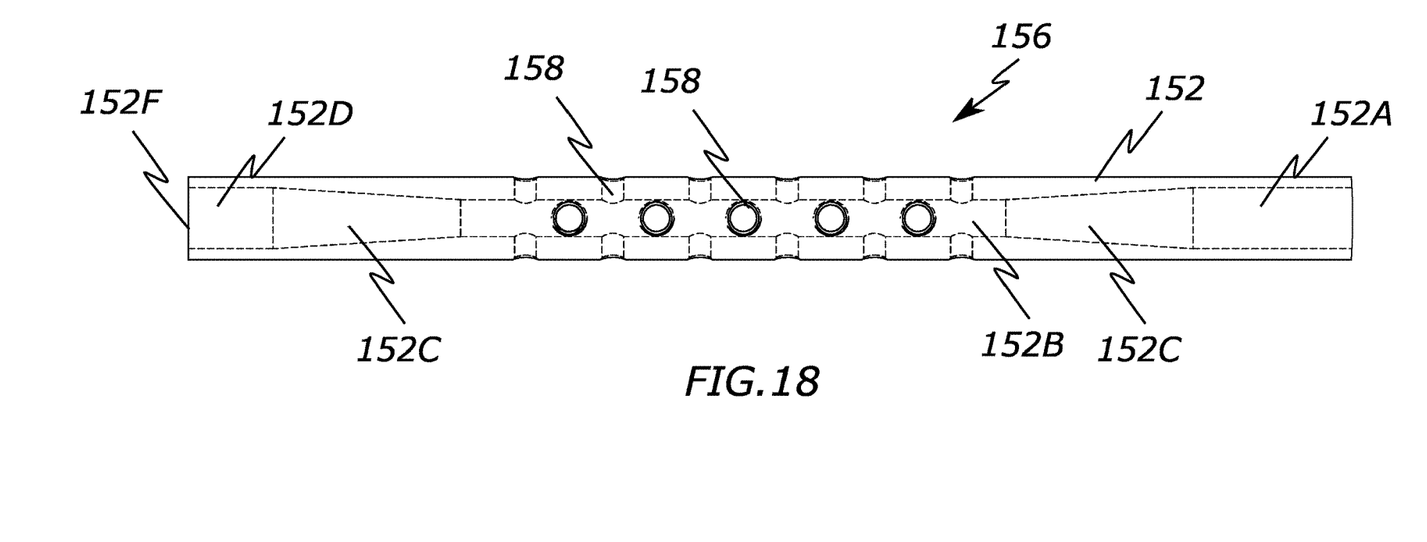
FIG. 18 is a perspective view of a catheter configured to create suction through side apertures at its distal end according to the present invention.

Similar to the prior embodiment, the distal portion 124 may include an angled or tapered surface 124A that creates a transition from the first diameter of the catheter shaft lumen 102A to the larger total diameter of lumens 124C and 124D. Additionally, as seen in FIG. 16, the proximal surface of the structure 124B can be tapered, increasing in diameter distally, to provide a smooth transition and reduce any potential turbulence.

Either embodiments of the catheters 100 or 120 may have similar methods of use. First, the catheter 100, 120 is advanced in a patient's vessel (e.g., via a guide sheath or via a guidewire) so that the distal portion 104, 124 is positioned in or near a desired target region (e.g., a desired area to occlude). Next, a fluid supply attached to or in communication with the catheter hub 106 is injected or otherwise pressurized into the lumen of the catheter hub 106, through the lumen 102A of the catheter shaft 102, through the distal portion 104, 124 and out of the opening of the distal end of the catheter 100, 120. As the fluid passes through the distal portion 104, 124, some fluid passes through the middle lumen 104D, 124D, and other fluid passes through the smaller lumens 104C, 124C, thereby creating a laminar fluid flow as the fluid exits.

In the examples shown with regard to catheters 100 and 120, the laminar fluid flow has a first middle portion and a second circumferential portion that surrounds the middle portion and comprises a plurality of laminar streams (or possibly a single laminar stream if a single lumen is used). In some configurations, the second circumferential portion may travel faster than the fluid flow of the first middle portion. Again, while any type of fluid can be used with the present catheter, it may be particularly helpful for use with occlusive agents (e.g., quickly solidifying liquid embolic agents or beads) and/or a liquid contrast agent.

As previously discussed, it can be difficult to deliver embolic agents to a location within a patient without those agents migrating to other areas of the vascular system and occluding non-target vessels. While this unintended occlusion is a problem for most embolic agents, it can be particularly challenging when using embolic beads.

For example, Trans-arterial Chemoembolization procedures (TACE) inject embolic beads containing a high amount of a chemotherapy agent in one or more vessels feeding a cancer mass. These beads can both occlude vessels leading to the cancer mass and deliver a relatively high amount of chemotherapy agent to the cancer mass. Beads such as Lifepearl/Hydropearl or Embospheres are commonly used for such procedures. However, as the beads are injected, they can reflux or move proximally backward in the vessels, resulting in the beads traveling to vessels that do not feed the target cancer mass and thereby resulting in possible complications.

In some circumstances, this reflux of embolic beads is reduced by first delivering microcoils to the location and then delivering the beads between the microcoils. However, it is still possible for some of the beads to escape and travel to other locations.

In some circumstances, a balloon from a balloon catheter can be inflated proximally of the delivery catheter (e.g., Embolx's Sniper balloon catheter). While the balloon may stop movement of the beads while inflated, once it is deflated the beads that have refluxed against the balloon are then free to migrate to other locations.

Specialty catheters with expandable nets or grates, such as the TriSalus' Surefire catheter, or Guerbet's Sequre catheter use filters or grates for capturing refluxed embolic beads. However, these specialty devices can be particularly expensive and, in some cases, can induce a vasospasm within the target vessel.

Previously discussed U.S. Pat. No. 10,398,875 has a plurality of openings at its distal end that are configured to direct fluid to areas surrounding the distal end of the catheter to attempt to create a fluid flow that blocks proximal reflux of embolic beads. However, this adjacent fluid flow may not always block reflux of beads and may create turbulence that may push some beads proximally to other areas of the vessel.

In contrast, some embodiments of this specification are directed to a delivery catheter that can both inject embolic beads (or other embolic materials) out its delivery opening of its main lumen and can suction or draw up embolic beads that have refluxed proximally through smaller apertures in the catheter's sidewall back into the main lumen. This may prevent the embolic beads from moving proximally beyond the sidewall apertures.

One approach to creating a suction or vacuum force through sidewall apertures of the catheter is to increase the speed of the fluid passing through the catheter's lumen adjacent to the sidewall apertures relative to the fluid speed more proximal in the catheter lumen. By accelerating the fluid speed at that location, a decrease in fluid pressure results, which causes a suction force or pressure differential relative to outside the catheter that thereby draws fluid from outside of the catheter into the sidewall apertures. This phenomenon is described by Bernoulli's principle or the Venturi effect, and allows for the recapture or scavenging of embolic beads (or other embolic agents) that have refluxed or moved proximally. There, the embolic beads move back into the main lumen of the catheter where they can again be delivered to the target area. Hence, this suction on the side of the catheter helps prevent the embolic beads from migrating further proximally to undesirable areas of the vasculature.

FIGS. 17-20 illustrate various views of a delivery catheter 150 that is generally similar to the previously described catheters of this specification, including a hub 154 with a thread 154A or other mechanism to attach to a source of embolic beads or other embolic agents, a catheter shaft 152 having at least one lumen therethrough, and a distal end portion 156. However, the distal end portion 156 is instead configured to create suction via the Venturi effect through one or more sidewall apertures 158 that connect the interior catheter lumen with the fluid outside of the catheter 150.

Generally, the Venturi effect of the catheter 150 is created by narrowing the lumen of the catheter. Specifically, a proximal region 152A of the catheter lumen extends from a proximal end of the catheter shaft 152 to the distal portion 156 and has a first, relatively large lumen diameter. As seen best in FIGS. 18 and 19, catheter shaft lumen begins decreasing or tapering in diameter distally at adjacent region 152C until it reaches region 152B, which may have a relatively uniform diameter that is smaller than that of the proximal region 152A of the catheter shaft 152.

Figure 19:
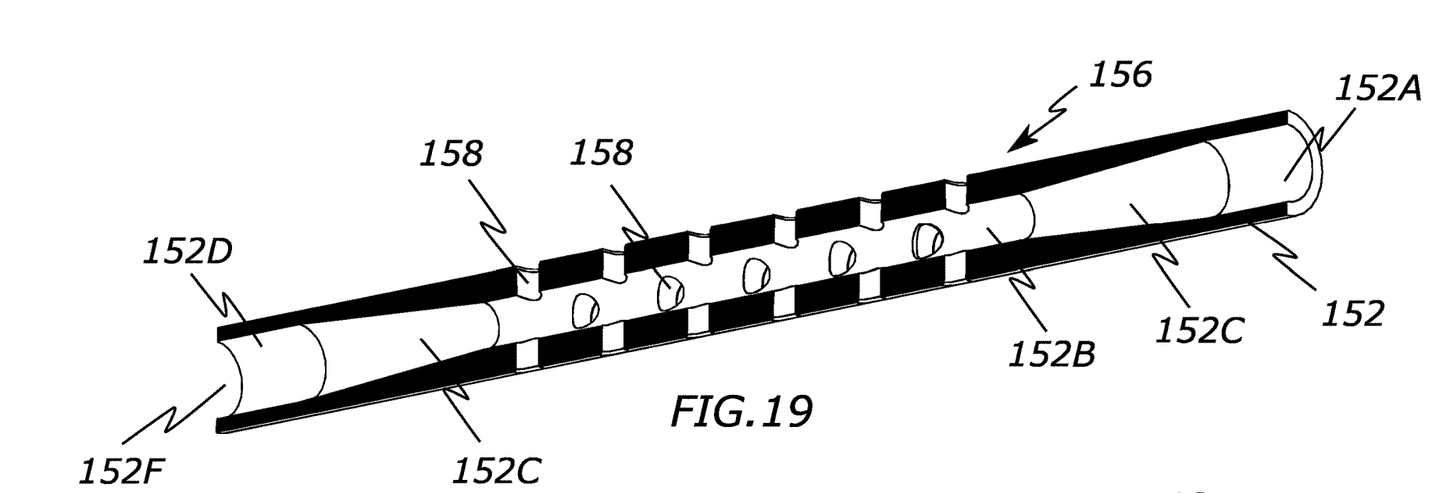
FIG. 19 is a cross-sectional view of a distal end of a catheter configured to create suction through side apertures at its distal end according to the present invention.

Optionally, the catheter shaft lumen begins to increase or taper distally through region 152C until it terminates with region 152D, which has a larger diameter than region 152B. This larger diameter region 152D may reduce the amount of backpressure that is created so as to thereby maintain the desired flow through the lumen and may also minimize the frictional flow pressure loss through the smaller diameter region 152B. Alternately, the smaller diameter of region 152B may be maintained until the very end of the catheter 150. The catheter shaft lumen ultimately terminates with the main delivery opening 152F through which fluid (e.g., saline, contrast) and embolic agents are ejected out from.

Figure 20:
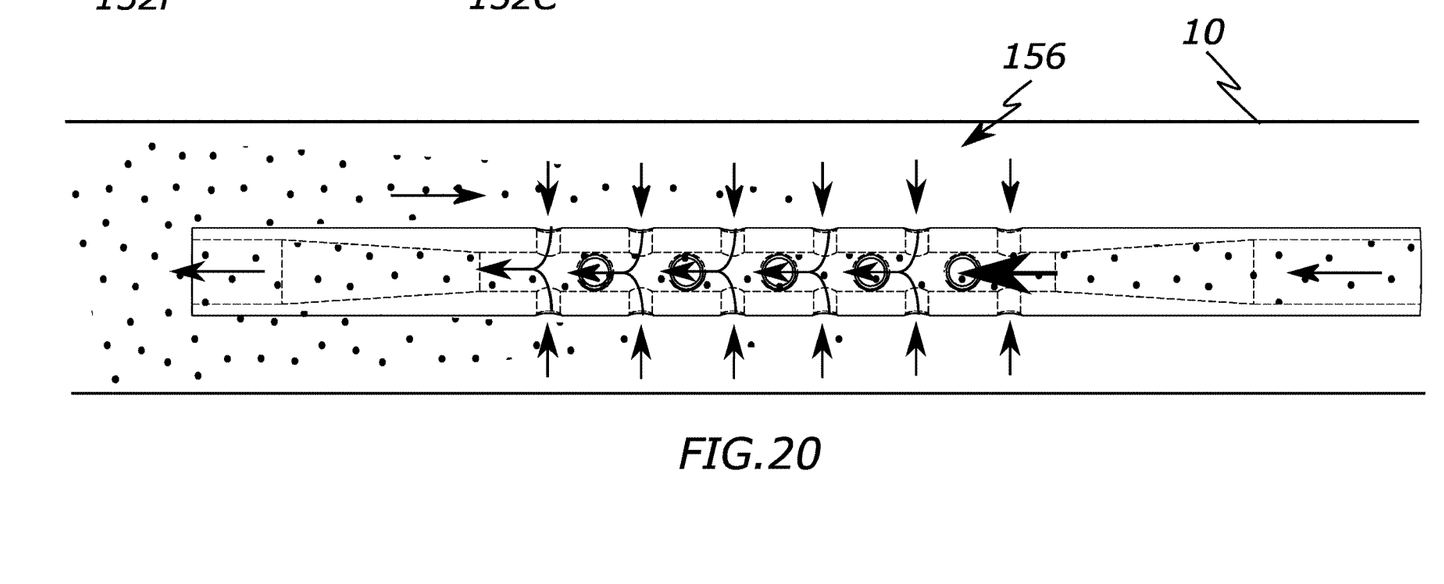
FIG. 20 is a cross-sectional view of a distal end of a catheter configured to create suction through side apertures at its distal end according to the present invention.

The fluid flow through the distal portion 156 of the catheter 150 can be seen best FIG. 20 within a vessel 10, where the arrows indicate the direction of the fluid flow. Fluid, including an embolic agent such as embolic beads seen in the figure, are injected into a lumen of the hub 154, passing into region 152A of the catheter lumen at a generally constant speed and pressure. As the fluid reaches the tapered region 152C and narrower region 152B, it increases in speed and decreases in pressure. This decreased pressure relative to the pressure outside the catheter creates suction through the one or more apertures 158 and into the catheter lumen. The fluid and embolic beads that are drawn into the catheter lumen are then pushed out through tapered region 152C and larger region 152D until it exits the distal end of the catheter 150. Hence, the embolic beads (depicted by black dots) are recaptured as they reflux or migrate proximally from a distal end of the catheter 150. This helps prevent the embolic beads from moving to an undesirable location elsewhere in the vasculature.

Figure 21:
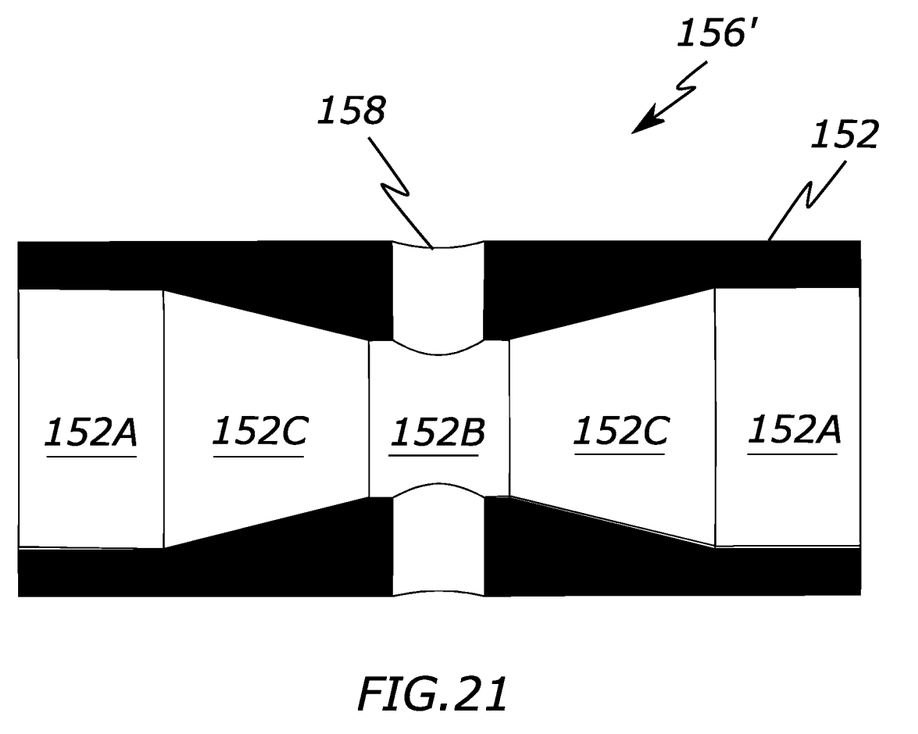
FIG. 21 is a cross-sectional view of a distal end of a catheter configured to create suction through side apertures at its distal end according to the present invention.

It is possible to have as few as one or two apertures 150 in the distal region, such as seen in the distal region 156' in FIG. 21, which has two apertures 158. However, including more than two apertures, as seen in FIGS. 17-20 may be desirable since they may provide more opportunities to scavenge the embolic beads. In that respect, the catheter 150 may include 1 to 50 apertures 158, for example, distributed along a length of the catheter shaft 152. More specifically, the catheter 150 may include 1, 2, 3, 4, 5, 6, 7, 8, 9, 10, 11, 12, 13, 14, 15, 16, 17, 18, 19, 20, or more apertures 158.

At a specific cross-sectional area, one or more apertures 158 may be included. For example, a specific cross-sectional area may only include two oppositely facing (i.e., circumferentially opposite) apertures 158 (i.e., apertures 158 are located at about 180 degrees from each other). In another example, a specific cross-sectional area may only include four apertures 158, each oppositely facing another aperture 158 (i.e., apertures 158 are located at about 90 degrees from each other).

The pattern of the apertures at a specific cross-sectional area may be repeated at various locations along the length of the distal region. For example, six longitudinally spaced positions may each have the same number of apertures oriented at the same rotational positions (e.g., 0, 90, 180, and 270-degrees). Alternately, the rotational orientations may alternate or change at different longitudinal positions. For example, the catheter 150 includes 11 longitudinal aperture locations with two oppositely oriented aperture 158 at each longitudinal position. However, each longitudinal position alternates between 0 and 180-degree aperture positions and 90 and 270-degree aperture positions. In another example, adjacent apertures may follow a longer aperture pattern, such as a first longitudinal location having a 0-degree aperture, a second longitudinal location having a 90-degree aperture, a third longitudinal location having a 180-degree aperture, and a fourth longitudinal location having a 270-degree aperture.

The embodiments of FIGS. 17-20 and 21 depict a single region 152B of reduced diameter and apertures 158. However, it is also possible to have a plurality of sections, similar to that shown in FIG. 21, along the length of the distal portion 156. For example, the distal portion 156 may include 2, 3, 4, 5, 6, 7, 8, or more sections similar to FIG. 21 that thereby alternates between larger and smaller diameters adjacent to apertures 158.

The diameter of the apertures 158 is preferably sized at least slightly larger than the embolic bead size being used in a procedure. For example, 100, 200, 300, and 400 micron embolic beads are popular bead sizes and therefore having an aperture diameter of at least 400 microns or about 405 to 420 microns (or larger) may be desirable to recapture those embolic beads. Alternately, the aperture diameter may be at least 5-10% larger than an embolic bead size (e.g., 100, 200, 300, or 400 microns), however much larger apertures are also possible and may address any clumping or adhering of the beads together.

Optionally, the apertures 158 may have a countersink or enlarged bevel surrounding the aperture 158 which may help direct each of the embolic particles into the aperture 158.

Preferably, the initial tapered region 152C is relatively gradual to prevent the embolic beads within the catheter lumen from clumping. In one example, the taper angle relative to the longitudinal axis of the lumen is within an inclusive range of about 5 and 25 degrees.

Generally, the Venturi Effect occurs under almost any constriction size. The smaller the constriction the faster the fluid typically moves and the greater the suction that is created. In that respect, a relatively larger size differential can be helpful. In one example, a reduction in diameter of in a range of about 30-70% (e.g., about 50%) may achieve particularly desirable results. In one more specific example, a standard 0.027" ID catheter has a constriction diameter of 0.016", which is a reduction in cross sectional area of about 65%, has a fluid flow applied at about 1 mL/s which generates a pressure gradient of about 250 mmHg (~5 psi). A reduction in cross sectional area of 56% in the same parameters as above may lead to a pressure gradient of about 150 mm Hg.

The lower bounds of this constriction may depend on the size of the guidewire needed for use with the catheter, at least in some circumstances that require a guidewire to pass through the lumen of the catheter initially. Typically, most catheter labs stock guidewires that as small as 0.014" to 0.016 though smaller guidewires exist. Hence, it may be helpful to limit the reduced diameter region to those sizes for practical use.

The catheter 150 can have several different sizes. For example, it can be a 2.8 F with an inner diameter of about 0.028" and an outer diameter of 0.038" where the reduced diameter inner diameter region 152B has a diameter of about 0.016" with an aperture size of about 0.010-0.015".

To achieve a desired Venturi effect that produces desired suction through the apertures 158, a sufficient amount of pressure must be pushed through the catheter 150. This may depend on the catheter and catheter lumen size, as well as the aperture 158 size. In one example, an injection pressure of at least 10 psi may be used to create the desired Venturi Effect, which is relatively small. By way of contrast, a 1 cc syringe with 75 N of force applied can create an injection pressure on the order of magnitude of about 350 psi.

A catheter that creates suction through side apertures via the Venturi effect may be a desirable approach since the scavenged embolic beads can be redirected back to the target location. However, other approaches without the Venturi effect may also be possible, such as having a separate dedicated aspiration lumen connected to a plurality of apertures.

Figure 22:
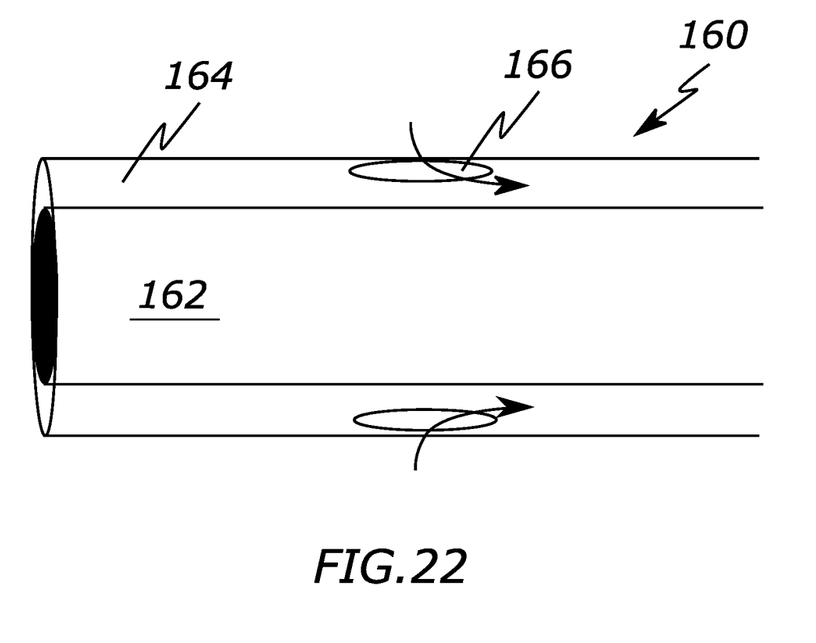
FIG. 22 is a cross-sectional view of a distal end of a catheter configured to create suction through side apertures at its distal end according to the present invention.

For example, as seen in FIG. 22, a catheter 160 may have two lumens; a main delivery lumen 162 through which the embolic beads and fluid (e.g., contrast and saline) are delivered, as well as a separate circumferential outer lumen 164 with one or a plurality of apertures 166 through which aspiration can be applied. In that respect, as the embolic beads are injected through the main delivery lumen 162, aspiration can be applied to the outer lumen 164 to suction any proximally refluxed beads.

In one embodiment, both the flow modifying structures of FIGS. 1-16 and the scavenging apertures of FIGS. 17-22 may be combined into a single catheter. In such an arrangement, the flow modifying structures are preferably located closest to the distal end and the scavenging apertures are located proximal of the flow modifying structures.

While specific embodiments have been disclosed, it is the intent of this specification that any of the features of any of the embodiments be mixed and matched with each other in any manner. Hence, the invention and claims should not be limited solely to specific embodiments shown, but also to any combination of the features discussed, without limitation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A catheter for delivering embolic agents, comprising:
   a catheter shaft;
   a delivery lumen within the catheter shaft; and,
   a fluid flow modifying structure within a distal portion of the delivery lumen comprising a central lumen and a plurality of outer lumens that are each located adjacent to the central lumen, each of the plurality of outer lumens being in fluid communication with the central lumen; and,
   wherein at least part of a length of each of the plurality of outer lumens form longitudinal channels that connect to the central lumen.

2. The catheter of claim 1, wherein the central lumen and the plurality of outer lumens branch off from a proximal portion of the delivery lumen.

3. The catheter of claim 1, wherein the plurality of outer lumens at least partially surround the central lumen.

4. The catheter of claim 1, wherein the plurality of outer lumens are each located adjacent to a circumference of the central lumen.

5. The catheter of claim 1, wherein the plurality of outer lumens each have a diameter that is smaller than a diameter of the central lumen.

6. The catheter of claim 1, wherein at least part of a length of the plurality of outer lumens forms discrete passages that are physically separate from the central lumen.

7. The catheter of claim 1, wherein the plurality of outer lumens all have the same diameter or have several different diameters.

8. The catheter of claim 1, wherein the central lumen and the plurality of outer lumens are all configured to eject fluid straight relative to a longitudinal axis of the catheter or wherein at least one of the central lumen or the plurality of outer lumens are configured to eject fluid along a trajectory non-parallel to the longitudinal axis of the catheter.

9. A catheter for delivering embolic agents, comprising:
   a catheter shaft;

a delivery lumen within the catheter shaft; the delivery lumen having a delivery opening at a distal end of the delivery lumen configured to eject fluid;

a reduced diameter region of the delivery lumen that has a uniform diameter along its length that is less than a diameter of a proximal region of the delivery lumen; and, at least one sidewall aperture located through a sidewall of the catheter shaft and into the reduced diameter region of the delivery lumen;

wherein the reduced diameter region and the at least one sidewall aperture are configured to create suction of fluid from outside of the catheter shaft, through the at least one sidewall aperture, and into the reduced diameter region when fluid is injected into a proximal portion of the delivery lumen.

10. The catheter of claim 9, wherein the at least one sidewall aperture further comprises a plurality of sidewall apertures.

11. The catheter of claim 10, wherein at least some of the plurality of sidewall apertures are distributed along a length of the catheter shaft.

12. The catheter of claim 10, wherein at least some of the plurality of sidewall apertures are positioned circumferentially opposite of each other.

13. The catheter of claim 10, wherein the plurality of sidewall apertures have a diameter sized to capture an embolic bead.

14. The catheter of claim 10, wherein the plurality of sidewall apertures have a diameter of at least 400 microns.

15. A method of delivering fluid within a patient, comprising:

positioning a distal end of a catheter within a vessel of a patient;

injecting fluid into a first lumen of the catheter;

passing the fluid through a fluid flow modifying structure within a distal portion of the first lumen, the fluid flow modifying structure comprising a central lumen and a plurality of outer lumens that are each located adjacent to the central lumen, each of the plurality of outer lumens being in fluid communication with the central lumen, wherein at least part of a length of each of the plurality of outer lumens form longitudinal channels that connect to the central lumen;

creating a laminar fluid flow out of a distal end of the catheter.

16. The method of claim 15, wherein passing the fluid through the fluid flow modifying structure comprises passing the fluid through the central lumen and at least one of the plurality of outer lumens.

17. A method of delivering embolic agents within a patient, comprising:

positioning a distal end of a catheter within a vessel of a patient;

injecting fluid containing embolic agents into a delivery lumen of the catheter;

passing the fluid through a reduced diameter region of the delivery lumen that has a uniform diameter along its length that is less than a diameter of a proximal region of the delivery lumen; and, recapturing at least some of the embolic agents by creating suction of fluid from outside of the catheter, through at least one sidewall aperture, and into the reduced diameter region when fluid is injected into a proximal portion of the delivery lumen.

18. The method of claim 17, wherein the at least one sidewall aperture comprises a plurality of sidewall apertures.

* * * * *